United States Patent [19]

Alaimo

[11] 3,980,664

[45] Sept. 14, 1976

[54] 1-[(5-NITRO-2-FUROYL)METHYL]-2(1H) PYRIDONE

[75] Inventor: Robert J. Alaimo, Norwich, N.Y.

[73] Assignee: Morton-Norwich Products, Inc., Norwich, N.Y.

[22] Filed: Jan. 2, 1976

[21] Appl. No.: 646,165

[52] U.S. Cl. ............................ 260/297 Z; 424/263
[51] Int. Cl.² ........................................ C07D 211/32
[58] Field of Search .................... 260/297 Z, 295 L

[56] References Cited
OTHER PUBLICATIONS

Takahashi et al, Chemical Abstracts vol. 53, cols. 8142 to 8143 (1959).

Abst. of Chem. Pharm. Bull. vol. 6, pp. 46–49 (1958).
Alberti, Gazz. Chim. Ital., vol. 86, pp. 1181 to 1194 (1956).
Mohrle et al, Monatash. Chemie, vol. 102, pp. 233 to 244 (1971).
Nesnow et al, J. Heterocyclic Chemistry, vol. 10, pp. 779 to 784 (1973).

*Primary Examiner*—John D. Randolph
*Attorney, Agent, or Firm*—Anthony J. Franze

[57] ABSTRACT

1-[(5-Nitro-2-furoyl)methyl]-2(1H) pyridone is an effective antimicrobial agent.

2 Claims, No Drawings

1-[(5-NITRO-2-FUROYL)METHYL]-2(1H) PYRIDONE

This invention is concerned with chemical compounds. More particularly it is concerned with 1-[(5-nitro-2-furoyl)methy]-2(1H) pyridone. This compound is an effective antibacterial agent and is adapted to be combined in the form of dusts, solutions, sprays, elixers and unguents to provide compositions suitable for the eradication or prevention of bacterial growth. It is capable of inhibiting the growth of both gram-negative and gram-positive bacteria when tested by the commonly used serial dilution technique as exemplified in the following table:

| Organism | Inhibiting Concentration mg/ml |
| --- | --- |
| S. aureus | 1.50 |
| E. coli | 6.25 |
| S. fecalis | 6.25 |
| S. typhosa | 1.50 |
| A. aerogenes | 25.00 |
| Corynebacterium liq. | 12.50 |
| Shigella flexneri | 3.10 |
| Proteus mirabilis | 25.00 |

The preparation of the compound of this invention is readily carried out by warming together a mixture of 2-methoxypyridine and bromomethyl 5-nitro-2-furyl ketone in acetone.

In order that this invention may be fully available to and understood by those skilled in the art, the following method of its manufacture is set forth.

To a solution of 2-methoxypyridine (45 g, 0.4 mole) in acetone (500 ml) was added bromomethyl 5-nitro-2-furyl ketone (93 g, 0.4 mole). The stirred mixture was heated in a warm water bath for about 2 hr, then allowed to stand overnight at room temperature. The solution was filtered and the product weighed 69 g (69%). Recrystallization from nitromethane provided analytical material which melted at 221°–223°.

Analysis Calcd. for $C_{11}H_8N_2O_5$ (Percent): C, 53,23; H, 3.25; N, 11.29; Found: C, 53.21; H, 3.13; N, 11.22

What is claimed is:
1. 1-[(5-nitro-2furoyl)methyl]-2(1H) pyridone.
2. The method for preparing the compound of claim 1 by reacting 2-methoxypyridine with bromomethyl 5-nitro-2-furyl ketone.

* * * * *